United States Patent [19]

Arnold et al.

[11] Patent Number: 4,801,543

[45] Date of Patent: * Jan. 31, 1989

[54] PROCESS AND DEVICE FOR THE DIFFERENTIATION OF PARTICLES IN A MEDIUM

[75] Inventors: William M. Arnold, Aachen; Ulrich Zimmermann, Hurtgenwald-Gey, both of Fed. Rep. of Germany

[73] Assignee: Kerforschungsanlage Julich, Fed. Rep. of Germany

[*] Notice: The portion of the term of this patent subsequent to Dec. 2, 2003 has been disclaimed.

[21] Appl. No.: 831,857

[22] Filed: Jul. 18, 1984

[30] Foreign Application Priority Data

Jul. 18, 1983 [DE] Fed. Rep. of Germany ....... 3325843

[51] Int. Cl.[4] ............................................. C12N 13/00
[52] U.S. Cl. ...................................... 435/173; 424/3;
435/4; 435/287; 436/149; 436/151; 436/806;
204/403; 204/411; 204/155
[58] Field of Search ................. 128/1.3; 424/3; 435/4,
435/173, 287; 436/149, 151, 806; 204/403, 411,
155, 231; 210/748

[56] References Cited

U.S. PATENT DOCUMENTS

| | | | |
|---|---|---|---|
| 3,418,500 | 12/1968 | Davis | 310/308 |
| 4,338,169 | 7/1982 | Bienvenu | 204/155 |

FOREIGN PATENT DOCUMENTS 1096280  6/1984  U.S.S.R. ............................ 435/173

OTHER PUBLICATIONS

Laboratory Equipment Digest, vol. 18, No. 10 (Oct. 1980), pp. 91–93.

Primary Examiner—Robert J. Warden
Assistant Examiner—Stephen C. Wieder
Attorney, Agent, or Firm—Lorusso & Loud

[57] ABSTRACT

Disclosed is a process and device for facilitating the differentiation of particles in a medium. The particles, which belong to at least two different groups of particles, are enclosed in a chamber bounded by electrodes which produce a rotating electrical field. A means for producing two rotating electrical fields having opposite directions of rotation and variable rotational frequency is provided to be attached to the electrodes. The particles exposed to the rotating electrical field forces with opposite directions of rotation can be differentiated on the basis of their rotational behavior.

20 Claims, 3 Drawing Sheets

PROCESS AND DEVICE FOR THE DIFFERENTIATION OF PARTICLES IN A MEDIUM

BACKGROUND OF THE INVENTION

This invention concerns a process for the differentiation of particles (particularly cells), belonging to at least two grous of particles in a medium, which can rotate around an axis of rotation parallel to the axis of rotation of a rotating electrical field.

It is known from Z. Naturforsch. 37 c, 908–915 (1982), "Rotating Field-Induced Rotation and Measurement of the Membrane Capacitance of Single Mesophyll Cells of Avena sativa", W. M. Arnold and U. Zimmermann, that individual cells, protoplasts in this case, can be brought into rotation in a rotating electrical field, which is produced by four electrodes, for example, with each being displaced from the others by 90 degrees. It is also known that individual cells of a specific species of cell can be set into maximum rotational speed at a specific frequency of the rotating field (the so-called characteristic frequency).

When using the known process, cells which have different characteristic rotational frequencies for a particular maximum rotational speed can be differentiated from one another by adjusting the frequency of the rotating field to the characteristic frequency of one group of cells. The different cells can then be differentiated from one another by their different rotational speeds. However, with this procedure in a specific case, the differentiation on the basis of the differing rotational speeds may be truly difficult, so that the difference can be recognized visually only with practice.

It is therefore a principal object of the present invention to provide a process which facilitates for the operator the differentiation of particles on the basis of their rotational behavior in comparison with known differentation procedure.

Another object of the present invention is to provide a procedure for differentiating particles which is also applicable to particles of a nonbiological type.

Still another object of the present invention is to provide a device for implementing the process.

SUMMARY OF THE INVENTION

The above objects are achieved pursuant to the present invention by exposing the articles, one group of which is distinguished by specific electrical and/or mechanical properties affecting the rotational behavior, to rotating electrical field forces with opposite directions of rotation in such a way that the particles of the one group of particles differ from the particles of the other group of particles in their rotational behavior.

For the execution of the process pursuant to the invention, an apparatus is provided in which at least three electrodes forming an intermediate space between themselves for a chamber containing the particles, especially cells, or forming a container, or extending into the chamber provided to hold the particles, are arranged in such a way that the intermediate space or the chamber is exposed to a rotating electrical field produced by the electrodes. A device, which can be attached to the electrodes, produces two rotating electrical fields with opposite directions of rotation and variable rotational frequency in each case. The intensity of the rotating fields is appropriately variable in this case. It should be in such a range that electrical field strengths of approximately 1 to 1000 V/cm are produced in the chamber. The frequency range should lie within the range between 1 Hz and 1 GHz. However, a range of 1 Hz to 500 kHz suffices in many applications.

These and other features and objects of the present invention will be more fully understood from the following detailed description which should be read in light of the accompanying drawings.

BRIEF DESCRIPTION OF THE DRAWINGS

Two embodiments of the apparatus pursuant to the invention are illustrated schematically in the drawing and are described in detail below. Diagrams are also provided in the drawing to clarify the process pursuant to the invention.

The drawing shows.

DETAILED DESCRIPTION OF THE PREFERRED EMBODIMENT

Figure 1:
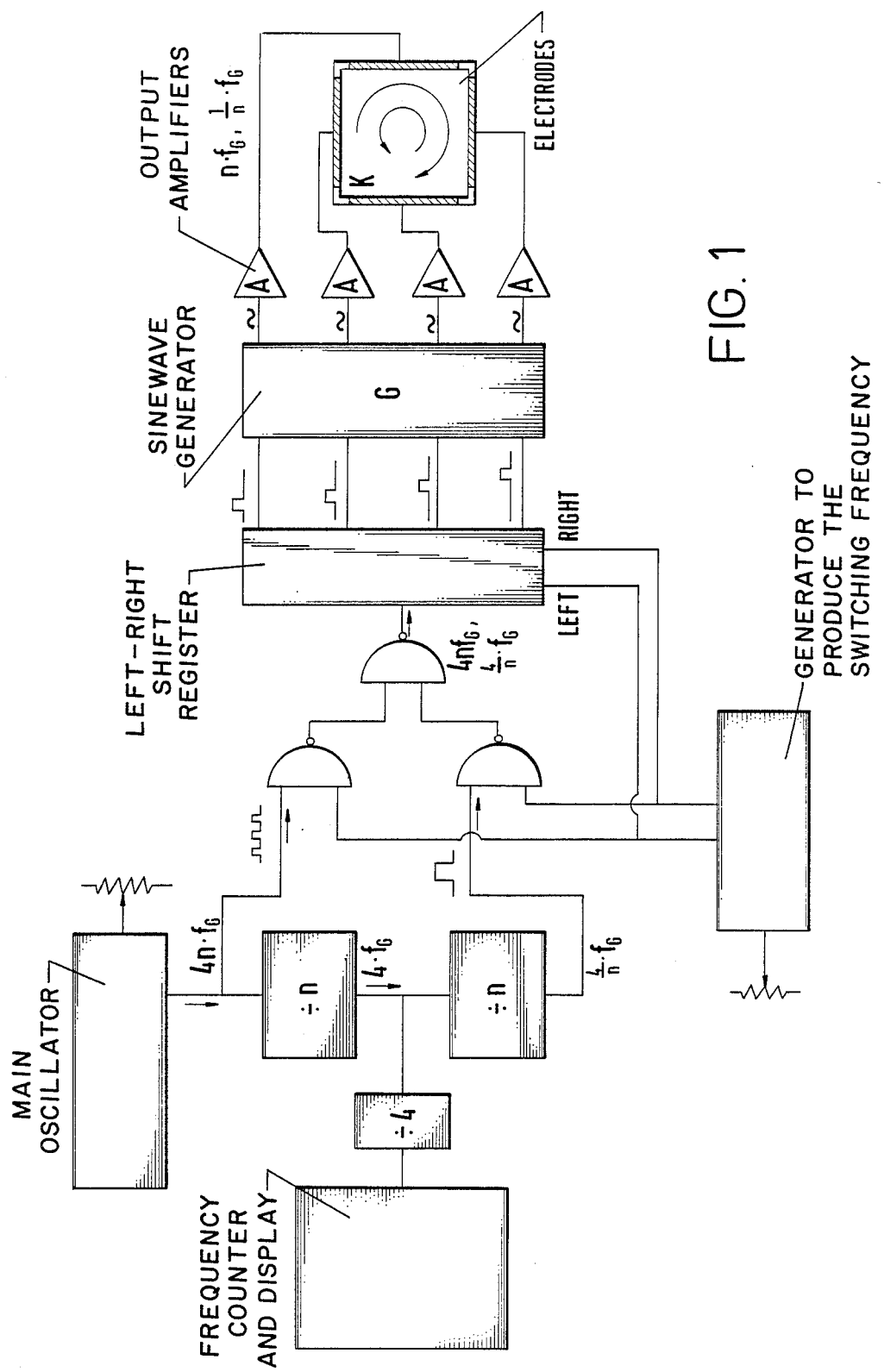
FIG. 1 is a schematic view of an embodiment of the apparatus of the present invention with four electrodes and a device connected to the electrodes which produces two rotating fields in opposite directions according to a specific switching sequence.

According to the present invention, a process is provided for facilitating the differentiation of particles in the medium. The particles (especially cells) are exposed to rotating electrical field forces with opposite directions of rotation in such a way that the rotational behavior of the particles of one group differs from the rotational behavior of the particles of another group.

The process pursuant to the invention is applicable to a broad area of technology, for example, where the problem involves the differentiation of particles of a powder and optical methods such as study under the microscope are inadequate. Thus, for example, it may be of interest to differentiate $BaTiO_3$ particles from $TiO_2$ particles also present as a result of the manufacturing process for $BaTiO_3$, and to be able to make an estimate of the percentage proportion of $TiO_2$ particles in a batch.

In the biological, pharmacological, and medical fields it is of interest to differentiate cells from one another. For example, when cells have a cell wall, such as plant cells, yeast cells, and bacteria, and when the cells have the same size, they cannot be differentiated under the microscope in spite of other differences. Thus, for example, cells of the same species and genus having a cell wall also cannot be differentiated under the microscope when their membrane has been damaged by detergents, environmental pollutants such as heavy metals, and the like. However, because of changes in the membrane of the cells, such cells have a different rotational behavior from that of undamaged cells of the same species. The damaged cells can therefore be differentiated from the undamaged cells on the basis of their different rotational behavior. Young cells of the same species can also be differentiated from old cells, or living cells from dead cells, by the use of their rotational behavior.

Cells of various bacterial strains which cannot be differentiated optically, or only with difficulty, can also be differentiated by the use of the process pursuant to the invention by the use of their different rotational behavior.

It has been found that nonbiological particles also have a maximum rotational speed at a characteristic rotational frequency. This characteristic frequency does indeed depend on other parameters, as it does for a specific species of cell, such as the environmental conditions for the particles, the conductivity of the medium in which the particles are located, and the temperature of the medium. However, only the different rotational behavior of the particles to be differentiated is involved in a differentiation measurement, with environmental conditions being otherwise identical. The conductivity of the medium, which appropriately lies in a range from 5 to 500 $\mu$S/cm, especially 5 to 50 $\mu$S/cm, is therefore of only subordinate importance for the differentiation of the particles themselves. In the case of cells to be differentiated, the temperature of the medium is adjusted primarily so that the cell functions are not impaired and the cells are not damaged.

A beneficial variation of the process pursuant to the invention, which makes possible a more precise determination of the differences in the rotational behavior of the particles, consists of choosing the magnitudes of the particular rotational frequency and the intensity of the two rotating fields so that the field forces acting either on the particles of one group or on the particles of the other group are just compensated for, and thus the particles exposed to the compensated rotating field forces are not set into rotation. The frequency of the rotating fields in this case is adjusted to different values, and the intensities of the rotating fields may also be different.

In the last-mentioned procedure, stationary particles can be differentiated from rotating particles, which leads to greater certainty in the differentiation in comparison with the process variation specified above. The natural spread of properties of particles, and thus also the spread in the rotational behaviour, can of course lead to the necessity of differentiating slowly rotating particles from rapidly rotating particles.

A simplification in the manipulation of the last-mentioned procedural variation results when the intensity of the rotating fields in the same, since only the rotational frequencies must then be changed to adjust to the optimal differentiation conditions. This variation of procedure is beneficially carried out in such a way that the rotational frequency of the one rotating field is 1/n times the characteristic rotational frequency which is determined for the particles not to be set into rotation, and the rotational frequency of the other rotating field is n times this characteristic frequency.

This implementation rule is based on the determination that the rotational speed of the particles depends logarithmically on the rotational frequency (with otherwise constant parameters). In the present case, this means that the rotational speed of the particles is the same as with rotational frequency by a specific number n. In the practical case of implementation of this procedural variation, however, this does not mean that the characteristic frequency must be known. Instead, when using a device in which two rotating fields are produced whose rotational frequencies correspond to the aforementioned conditions in each case by the choice of a specific rotational frequency, it is merely necessary to vary the "specific" rotational frequency until an adjustment of the rotational frequency is reached which corresponds to the characteristic rotational frequency, and at which the particles of the one group stop rotating. In this way, the particles to be differentiated can be readily recognized.

Another very beneficial procedural variation of the process pursuant to the invention, in the execution of which the recognition of the different rotational behavior of the cells is facilitated even further in comparison with the procedural variations described up to now, consists of choosing the magnitudes of the rotational frequency and of the intensities of the rotating fields in such a way that the resulting field forces act differently on the particles to the extent that the particles belonging to the different groups rotate in opposite directions. It is also appropriate with this procedural variation for the rotating electrical field with opposite directions of rotation to have the same intensity.

It is beneficial also in the last-mentioned procedure to proceed so that the rotational frequency of the one rotating field is 1/n times a frequency which lies between the characteristic frequencies determined for the different groups of particles, and the rotational frequency of the other rotating field is n times this frequency. For the reasons specified above, it is also unnecessary in this case for the specialist to know the characteristic rotational frequencies of the particles to be differentiated, since he arrives at an adjustment of the two rotating fields by varying the "specific" rotational frequency directly, at which the particles to be differentiated rotate in opposite directions.

For executing the various procedural variations, it can be appropriate for the rotating electrical fields, which rotate in opposite directions, to act in succession on the particles, with the switching frequency being so high that no interfering oscillations of the particles occur. Since the switching frequency is in the kHz range, oscillations of the particles can actually not be recognized visually, but they can be manifest in a disturbing lack of definition of the particle contours. These interferences caused by the oscillations should be avoided by the selection of a sufficiently high switching frequency.

FIG. 3 diagrammatically illustrates the variations of the process pursuant to the invention, in which the particles are exposed to the forces of two rotating fields whose frequencies are n and 1/n times an adjustable generator frequency.

The curve shape shown in Diagrams a through c of FIG. 3 (logarithmic dependence of the frequency of the rotating field acting on a particle on the angular momentum or on the rotational speed of the particle) applies here to the rotation of the particle under the influence of a rotating field. The maximum rotational speed of the particle set into rotation by the rotating field, as seen from the illustration a, is at the frequency $f_c$. The frequencies of the two rotating fields, which correspond to n or 1/n times the frequency $f_c$, are at the marks above and below the frequency $f_c$.

Figure 3A:
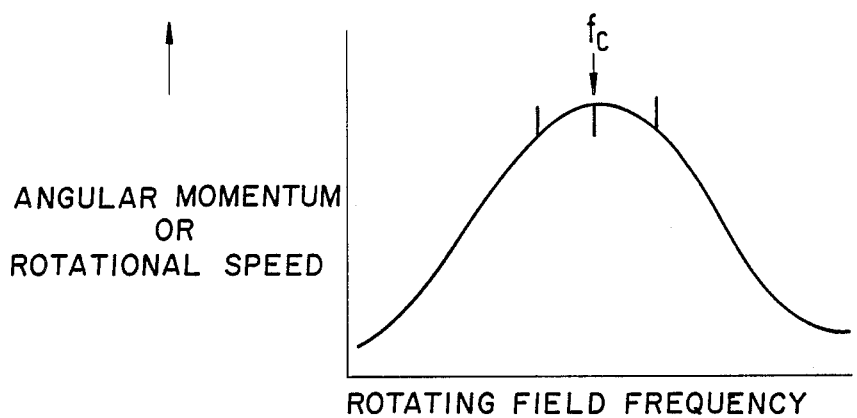

If the frequency $f_G$ of the generator corresponding to the illustration in FIG. 3a is chosen to be equal to the characteristic frequency $f_c$ for the particle, then the forces of the two rotating fields compensate for one another. The particle remains at rest.

Figure 3B:
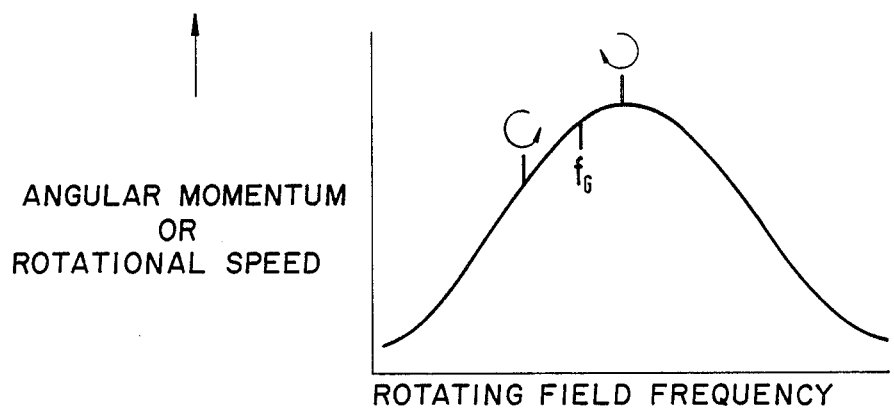
Figure 3C:
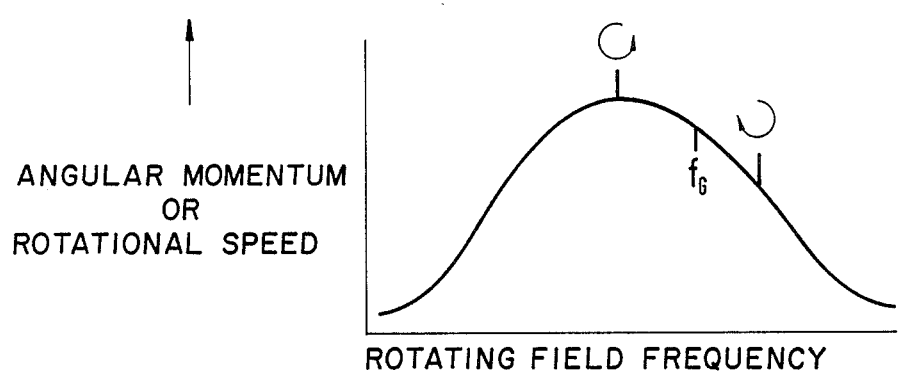

At the different settings of the generator frequency $f_G$ shown in FIGS. 3b through 3c, the particle rotates under the influence of rotating fields with different directions of rotation which do not compensate for one another.

Figure 3D:
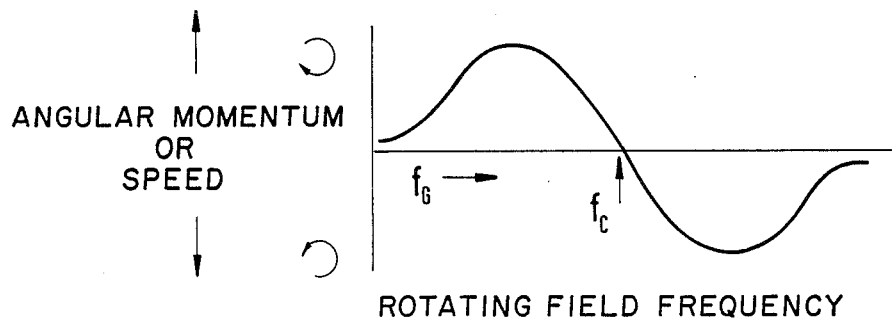

The rotational behavior of the particle is illustrated in FIG. 3d as a function of the frequency of the generator (with synchronized frequencies of the two rotating fields in each case). As seen from the diagram, the particle rotates above or below the frequency $f_c$ with difference directions of rotation.

According to the present invention, an apparatus is also provided for facilitating the differentiation of particles in a medium. The apparatus includes at leat three electrodes which either form an intermediate space between themselves for a chamber containing the particles, form a container, or extend into a chamber provided to hold the particles. These electrodes are arranged in such a way that the intermediate space or the chamber is exposed to a rotating electrical field produced by the electrodes. A device, which can be attached to the electrodes, produces two rotating electrical fields with opposite directions of rotation and variable rotational frequency in each case. The intensity of the rotating field is appropriately variable, and it should be in such a range that electrical field strengths of approximately 1 to 1000 V/cm are produced in the chamber. The frequency range should lie between 1 Hz and 1 GHz for most applications. However, a range of 1 Hz to 500 kHz is usually sufficient.

Another appropriate form of embodiment of the apparatus pursuant to the invention consists of the apparatus being designed so that the electrical voltages producing the two rotating fields are applied alternately to all of the electrodes in rapid sequence.

If at least six electrodes are present, then an appropriate form of embodiment of the apparatus can consist of the electrical voltages producing the two rotating fields being applied to different electrodes, at least three in number in each case. In this case, the two rotating fields do not need to be switched in alternately. Also beneficial is an embodiment of the apparatus pursuant to the invention in which the apparatus is designed so that upon selection of a specific rotational frequency, the apparatus produces two electrical voltages generating the two rotating fields, with the frequency of the one rotating field being 1/n times the specific rotational frequency and the frequency of the other rotating field being n times this frequency, and with the intensity of the two rotating fields being the same.

In this embodiment of the apparatus pursuant to the invention, use is made of the logarithmic dependence of the rotational speed of the particles on the rotational frequency. It is distinguished by a particularly easy manipulation, since only a single frequency needs to be varied, which is then adjusted, depending on the procedural variation to be carried out, to the characteristic frequency of one of the two groups of particles to be differentiated or to a rotational frequency between the characteristic rotational frequencies of the two groups to be differentiated.

In the apparatus just described, it is also appropriate for the apparatus to be designed so that the number n can be selected within a prescribed range, which lies perhaps between 1 and 50. The smallest value which can be used for n is greater than 1.

It is appropriate for the rotating electrical fields to be produced with sinusoidal voltages. However, it is also directly possible to produce the rotating fields by square-wave voltages or by pulsed voltages, or voltages of another form.

A special use of the apparatus pursuant to the invention consists of the differentiation of cells secreting cellular substances such as proteins and/or glycoproteins, hormones, or so-called growth factors, from cells of the same species or genus which do not secrete cellular substances.

This special use of the device is based on the discovery that cells which secrete cellular substances such as proteins and/or glycoproteins, or hormones, or growth factors, show a rotational behavior in a rotating electrical field different from that of cells of the same species or genus which do not secrete. This difference can be attributed to changes in the membrane of the cells.

In a number of applications in the biological, pharmacological, and medical field, there exists a need to be able to differentiate cells secreting cellular substances from cells of the same species and genus. Thus, for example, it is of considerable importance for the production of monoclonal antibodies, to differentiate lymphocytes stimulated for the formation and release of antibodies in a suspension containing stimulated lymphocytes and unstimulated lymphocyte. Certain lymphocytes form antibodies (glycoproteins) against foreign substances in the organism, for example against a foreign protein, which has been injected into the bloodstream. If such lymphocytes stimulated for the formation and release of antibodies are fused with a tumor cell, such as a myeloma cell, there is a chance that a so-called hybridoma cell will be formed which has the properties of both parent components. This cell produces antibodies, specifically only against the foreign substance involved (so-called monoclonal antibody). It is practically immortal and can multiply permanently in nutrient media, in contrast to a normal differentiated cell such as the lymphocyte.

However, since only a very small number of the many lymphocytes found in the lymphatic system are stimulated and since only the stimulated lymphocytes should be presented for the fusion if possible, the stimulated lymphocytes must be separated from the unstimulated lymphocytes in a selection process. It is however, difficult to recognize the stimulated lymphocytes, since they do not differ from the unstimulated lymphocytes under the microscope.

As another example, it might be mentioned also that some micro-organisms are able to lyse living cultured yeasts by secretion of certain cellular substances (primarily glycoproteins). These toxins are called "killer factors". "Killer yeasts" can cause difficulties in the production of beer. Even with a low degree of contamination, they cause changes of the fermentation and of the quality of the beer.

The existence and consequences of killer reactions have been established in brewery yeasts, wine yeast, and baking yeasts, as well as in other species of cell genera, such as Hansenula, Pichia, Deberyomyces, Kluyveromyces, Candida, and Torulopsis.

In the cases mentioned and many others, the problem is first to recognize the secreting cells in order to be able to initiate other measures. These can consist, for example in the case of the stimulated lymphocytes, of then separating out these cells. In the case of the killer yeast cells, the recognition of such cells initially is used for monitoring the fermentation process. This in turn can lead to the introduction of measures to void the contamination.

Beyond this, the device pursuant to the invention can be used beneficially for the measurement of electrical variables, and optionally mechanical variables which can be derived from these, which determine the rotational behavior of particles of biological and nonbiological types. Such variables in the case of cells, for example, are the characteristic rotational frequency, and when the diameter of the cells is known, their membrane capacity, the membrane resistance, and the internal conductivity of the cells. On the basis of these variables to be measured, for example, the harmful effects of environmental substances on the cells can also be recognized.

With nonbiological particles it can be of interest to determine the homogeneity of the particles by using the measurement of the dielectric constant and of the specific resistance. In the case of particles which have a cavity, information concerning the inside diameter of the particles can be obtained on the basis of the rotational behavior of the particles.

In the production of powder from $BaTiO_3$, for example, information concerning the density of the particles can be obtained, and thus the dielectric constant of a batch of the particles, by measuring the characteristic frequency, which makes possible a quality control.

The apparatus illustrated in FIG. 1 consists of a chamber K with four electrodes and a device connected to the electrode for producing two rotating fields in opposite directions.

The four electrodes are arranged on a base plate made of electrically nonconductive material, not shown in the drawing, in such a way that they form the lateral walls of the chamber K provided to hold the particles, such as cells. The electrodes are cemented to one another at the corners of the chamber, and to the base plate, by means of an electrically insulating adhesive.

The electrodes consisting of platinum foil are connected as shown in FIG. 1 to the output amplifiers V of the sine wave generator G. As also seen in FIG. 1, besides the sine wave generator G and its output amplifiers V, the device also consists of other units which are used to produce two voltages shifted by 90° in phase in each case for the production of the two rotating fields in opposite directions. Starting from the main oscillator, whose frequency is adjustable, a voltage sequence of an n-fold and a 1/n-fold frequency is thus produced. Corresponding to the set switching frequency of the "generator for the production of the switching frequency", the two voltage sequences are supplied alternately to the electrodes.

Figure 2:
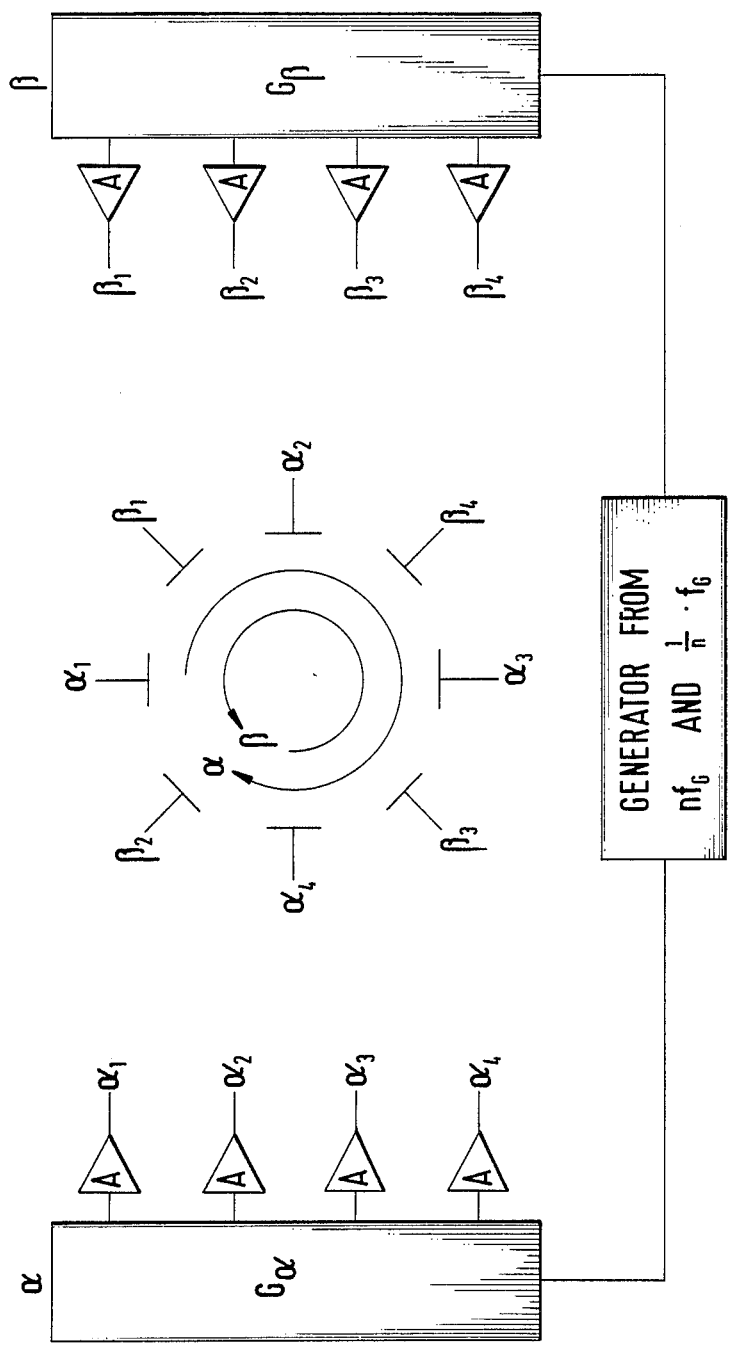
FIG. 2 is a schematic view of an embodiment of the apparatus of the present invention with eight electrodes and a device connected to the electrodes by means of which two constantly applied rotating fields rotating in opposite directions are produced by four electrodes in each case, FIG. 3 diagrammatically illustrates the execution of one variation of the process pursuant to the present invention.

In the apparatus illustrated in FIG. 2, there are a total of eight electrodes. These form an intermediate space in which a chamber is provided, not shown in the drawing. The electrodes are connected to the output amplifiers V of a generator $G_\alpha$ corresponding to the designations $\alpha 1$ to $\alpha 4$, and to the output amplifiers of a generator $G_\beta$ according to the designations $\beta_1$ to $\beta_4$. The voltages provided by the amplifiers are each shifted by 90 degrees, so that the directions of rotation of the two rotating fields shown in the drawing by arrows are produced with the connection provided for the electrodes to the output amplifiers. The voltages produced by the generators $G_\alpha$ and $G_\beta$ are sinusoidal. Their frequencies correspond to n or 1/n times an adjustable generator frequency $f_G$. The number n can be adjusted through the "generator of $(1/n)f_G$ and $nf_G$".

In general, concerning the following examples 1 and 2:

Stimulated B-lymphocytes were produced by injecting a mouse with sheep erythrocytes. The lymphocyte fraction taken from the mouse contained the stimulated lymphocytes together with unstimulated lymphocytes.

The lymphocyte fraction was placed in a bed of erythrocytes from sheep and later the stimulated lymphocytes, i.e., the lymphocytes secreting the antiody, were taken again by micropipette. The stimulated lymphocytes in this case could be recognized by the fact that a group of lysed erythrocytes had formed around them (according to the method described in the "Annales of Institute Pasteur, 1975" (Zagury and Coworkers)).

In this way, stimulated lymphocytes which secreted an antibody against the erythrocytes of sheep were obtained. Some of these stimulated lymphocytes were mixed with at least the same amount of unstimulated lymphocytes, which has also been taken from the erythrocyte bed by micropipette.

The mixture of lymphocytes, before it was placed in the rotation chamber K, was washed three times in a medium of low conductivity (0.3M mannitol with traces of sodium chloride as electrolyte).

The following examples were carried out be means of a device of the type illustrated in FIG. 1.

EXAMPLE 1

Differentiation of stimulated and unstimulated lymphocytes

Approximately 10 $\mu$l of a suspension containing the mixture of lymphocytes was placed in the rotation chamber K. The conductivity of the suspension was 18.4 $\mu$S/cm, and the temperature was 35° C. The suspension was exposed to a rotating electrical field with an intensity of approximately 100 V/cm. The frequency of the two rotating fields in each case was 2 times and $\frac{1}{2}$ times the set frequency of the generator (or of the oscillator).

The stimulated lymphocytes could be recognized under the microscope by the fact that they did not rotate at a rotational frequency of 38.2±5.5 kHz. They could thus be differentiated from the other lymphocytes, which did not rotate at a rotational frequency of approximately 24.5±4.8 kHz.

When the generator frequency was set at a value between the two indicated values, the different lymphocytes rotated in opposite directions.

The lymphocytes recognized as stimulated lymphocytes on the basis of their rotational behavior were removed from the rotation chamber by micropipette and were again placed in a bed of sheep erythrocytes for a check. The check confirmed that they were stimulated lymphocytes.

EXAMPLE 2

Differentiation of stimulated and unstimulated lymphocytes

As described in Example 1, a mixture of stimulated and unstimulated lymphocytes was exposed to a rotating electrical field. The conductivity of the suspension containing the lymphocytes, however, was 5.2 $\mu$S/cm.

In this case also, the stimulated lymphocytes were recognized by their rotational behavior. The corresponding rotational frequency was approximately 12.3±2.8 kHz. The rotational frequency at which the unstimulated lymphocytes did not rotate was approximately 7.1±1.1 kHz.

EXAMPLE 3

Differentiation of living and dead yeast cells

Yeast cells, *Saccharomyces cerevisiae* (Strain 93), were placed from a nutrient medium in distilled water. Some of the yeast cells were heated at 85° C. for 5 minutes. These cells were then centrifuged and washed. A fraction of the heated yeast cells were mixed with untreated yeast cells, and no difference could be recognized under the microscope.

The mixture was placed in a solution whose conductivity was 2 $\mu$S/cm. The temperature was 20° C. Approximately 10 $\mu$l of the solution containing the cell mixture was placed in the rotation chamber and exposed to the two rotating electrical fields (n=2). The heated (dead) cells could be recognized under the microscope by their rotational behavior and could be differentiated from the untreated cells. The characteristic frequency for the heated cells was at 500±200 kHz, and that for the untreated cells was at a generator frequency $\geq$ 3 MHz.

In a control test, in which only one group of cells in each case was exposed to the rotating electrical field in the rotation chamber, onlyone of the indicated characteristic frequencies could be measured in each case.

EXAMPLE 4

Differentiation of living and dead bacterial cells

The experiment was made with cells of *Bacillus megaterium*. These cells have the characteristic of joining into chains (consisting of mother and daughter cells). In executing the process, the rotation of a chain of cells is therefore observed under the microscope.

Some of the cells were heated to 85° C. for 5 minutes. The chains persisted.

As described in Example 3, a mixture of heated and untreated cells was prepared. This mixture thus contained chains of living cells along with chains of dead cells. The mixture was placed in a sodium chloride solution (conductivity 260 $\mu$S/cm, temperature 20° C.) No difference could be recognized in the cells in the solution under the microscope.

Approximately 10 $\mu$l of the solution containing the cell mixture was placed in the rotation chamber and exposed to the two rotating electrical fields (n=2). The differently treated cells could then be recognized and differentiated by their rotational behavior. The characteristic frequency for the heated cell chains was 70 Hz, and that for the untreated cell chains was 35 Hz. A control measurment of the type described in Example 3 confirmed the result.

EXAMPLE 5

Differentiation of cells damaged by detergents from undamaged cells

Cells of *Saccharomyces cerevisiae* (Strain 93) were placed in a starting solution consisting of distilled water. Some of these were placed in a solution for 1 hour which contained 0.09% HDTAB (hexadecyltrimethylammonium bromide). The cells were then centrifuged and washed four times in distilled water.

A mixture of treated and untreated cells was again prepared (conductivity of the solution 2 $\mu$S/cm, temperature 20° C.). The cells could not be differentiated visually under the microscope, and a study in the rotation chamber showed different rotational behavior for the two groups of cells.

The characteristic frequency for the cells damaged by the detergent was 80±10 kHz, while the characteristic frequency of the undamaged cells was $\geq$ 3 MHz. It was found here that the rotation of the cells was in the same direction as the field forces acting on them.

For a different frequency range in which the particles rotated in the direction opposite to that of the rotating field acting on them, a characteristic frequency of 200 Hz was found for the damaged cells and a frequency of 10±2 kHz for the undamaged cells. A control measurement of the type described in Example 3 confirmed the result.

EXAMPLE 6

Differentiation of cells damaged by an environmental pollutant from undamaged cells Some of the cells from the starting solution described in Example 5 were placed for 1 hour in a solution which contained 100 ppm of HgCl$_2$. After centrifuging the cells and washing them four times, a mixture of treated and untreated cells was again prepared. The conductivity of the solution containing the mixture was 2 $\mu$S/cm, and the temperature was 20° C.

No difference between the cells in the mixture could be recognized under the microscope, but a study in the rotation chamber showed different rotational behavior of the two groups of cells. The characteristic frequency for the damaged cells was 120±20 kHz, and the characteristic frequency of the undamaged cells was 400 to 500 Hz. A control measurement of the type described in Example 3 confirmed the result.

EXAMPLE 7

Differentiation of yeast cells of two different genera

A mixture of yeast cells *Saccharomyces cerevisiae* (Strain 93) and Hansenula II sp (unknown species) was prepared. Under the microscope, the cells belonging to the different groups could be differentiated from one another, but only with difficulty.

The cell mixture was placed in distilled water (conductivity 2 $\mu$S/cm, temperature 20° C.). The cells could be differentiated from one another by their rotational behavior. The characteristic frequency for the cells of Hansenula II was 100–300 kHz, and the characteristic frequency for the cells of *Saccharomyces cerevisiae* was at $\geq$ 3 MHz.

EXAMPLE 8

Differentiation of particles of nonbiological type

A mixture of particles consisting of BaTiO$_3$ and TiO$_2$ with an average particle diameter of 2 $\mu$m was washed five times in distilled water and then placed in water which contained traces of NaCl (conductivity 2.6 $\mu$S/cm, temperature 20° C.)

The particles could be differentiated from one another by their rotatonal behavior. The characteristic frequency of the BaTiO$_3$ particles was 7.8±1.0 kHz, and that of the TiO$_2$ particles was 135±10 kHz. The different particles rotated in opposite directions, and a control test confirmed the result.

It should also be noted that BaTiO$_3$ has a dielectric constant of approximately 2000, while that of TiO$_2$, on the other hand, is approximately 100.

EXAMPLE 9

Differentiation of particles of nonbiological type

Corresponding to Example 8, mixture of BaTiO$_3$ and TiO$_2$ particles was studied. The conductivity of the solution containing the mixture was 5.2 μS/cm, and the temperature was 20° C. The characteristic frequency for the BaTiO$_3$ particles was 16.0±2.2 kHz, and that for the TiO$_2$ particles was 280±25 kHz. The particles also rotated in opposite directions in this case. A control test confirmed the result.

The foregoing invention has been described with reference to its preferred embodiments. Although variations and modifications will occur to those skilled in the art, it is intended that such variations and modifications fall within the scope of the appended claims.

What is claimed is:

1. A process for the differentiation of particles, particularly cells, belonging to at least two groups of particles in a medium, said particles being a capable of rotating around an axis of rotation of a rotating electric field, comprising the steps of:
exposing the particles, one of which is distinguished from a second other group by specific electrical and mechanical properties or both which affect the rotational behavior, to two stimultaneous rotating electrical field forces with opposite directions of rotation in such a way that the particles of the one group of particles are differentiated from the particles of the second other group of particles by their rotational behavior.

2. The process for the differentiation of particles of claim 1 wherein the particular rotational frequency and the intensity of the rotating fields are chosen to be of such magnitudes that the field forces of the second other group are just balanced such that one of the groups of particles exposed to the balanced rotational field forces are not set into rotation.

3. The process for the differentiation of particles of claim 2 wherein the rotating electrical fields showing the opposite directions of rotation have the same intensity.

4. The process for the differentiation of particles of claim 3 wherein the rotational frequency of the one field is 1/n times the characteristic rotational frequency and the rotational frequency of the other rotating field is n times the characteristic rotational frequency which is determined for the particles not be set into rotation wherein n is number between 1 and 50.

5. The process for the differentiation of particles of claim 1 wherein the rotational frequency and the intensity of the rotating fields are selected to have magnitudes such that the resulting rotating field forces have different effects on the particles to the extent that the particles belonging to different groups rotate in different directions.

6. The process for the differentiation of particles of claim 5 wherein the rotating electrical fields showing opposite directions of rotation have the same intensity.

7. The process for differentiation of particles of claim 6 wherein the rotational frequency of the one rotating field is 1/n times a frequency which lies between the characteristic frequencies determined for the different groups of particles, and the frequency of the second rotating field is n times the frequency which lies between the characteristics frequencies determined for the different groups of particles wherein n is a number between 1 and 50.

8. The process for the differentiation of particles of claim 1 wherein the rotating electrical fields with opposite directions act on the field successively, with the frequency that results from switching from one rotating electric field to the second rotating electric field being of such magnitude that no interfering oscillations of the particles occur.

9. The process for the differentiation of particles of claim 1 wherein the electrical fields rotating in opposite directions act simultaneously on the particles.

10. An apparatus for use in the differentiation of particles comprising;
a chamber containing the particles;
at least three electrodes arranged in such a way that the chamber is exposed to a rotating electric field produced by the electrodes, and
means for producing two simultaneous rotating electrical fields with opposite directions of rotation and variable rotational frequencies in each case, said means being connected to said electrodes.

11. The apparatus for differentiating particles of claim 10 wherein said electrodes produce a rotating field the intensity of which is variable.

12. The apparatus for differentiating particles of claim 10 wherein further comprising means for alternately applying the electrical voltages producing the two rotating fields to all electrodes in sequence.

13. The apparatus for differentiating particles of claim 10 wherein there are at least six electrodes, and wherein the electrical voltages producing the two rotating fields are applied to different electrodes, at least three in number in each case.

14. The apparatus for differentiating particles of claim 10 wherein upon selection of a sepcific rotational frequency the apparatus produces voltages generating the two rotating fields, with the frequency of the one rotating field being 1/n times the specific rotational frequency and the frequency of the other rotating field being n times this frequency, and with the intensity of the two rotating fields being the same.

15. The apparatus for differentiating particles of claim 14 wherein the number n is 2.

16. The apparatus for differentiating particles of claim 10 wherein the electrical voltages producing the rotating fields are sinusoidal voltages.

17. The apparatus for differentiating particles of claim 10 further comprising means for processing cells in order to differentiate cells secreting cellular substances selected from the group consisting of proteins, glycoproteins, hormones, and growth factors, from cells of the same species or genus which do not secrete cellular substances.

18. The apparatus for differentiating particles of claims 10 further comprising means for measuring the electrical variables, and optionally the mechanical variables which can be derived from said electrical variables which determine the rotational behavior of particles.

19. The apparatus for differentiating particles of claim 10 wherein said at least three electrodes are walls of said chamber.

20. The apparatus for differentiating particles of claim 10 wherein said electrodes extend into the chamber.

* * * * *